United States Patent
Neuhauser

(10) Patent No.: US 10,024,830 B2
(45) Date of Patent: Jul. 17, 2018

(54) DETECTOR ARRANGEMENT

(71) Applicant: Siemens Aktiengesellschaft, Munich (DE)

(72) Inventor: Thomas Neuhauser, Bartlesville, OK (US)

(73) Assignee: Siemens Aktiengesellschaft, Munich (DE)

( * ) Notice: Subject to any disclaimer, the term of this patent is extended or adjusted under 35 U.S.C. 154(b) by 167 days.

(21) Appl. No.: 15/172,713

(22) Filed: Jun. 3, 2016

(65) Prior Publication Data

US 2016/0363566 A1 Dec. 15, 2016

(30) Foreign Application Priority Data

Jun. 9, 2015 (DE) .................. 10 2015 210 548

(51) Int. Cl.
*G01N 30/66* (2006.01)
*G01N 30/02* (2006.01)
*G01N 30/78* (2006.01)

(52) U.S. Cl.
CPC ............. *G01N 30/66* (2013.01); *G01N 30/78* (2013.01); *G01N 2030/025* (2013.01)

(58) Field of Classification Search
CPC ......... G01N 27/18; G01N 30/66; G01N 30/78
USPC ........................................................ 73/23.4
See application file for complete search history.

(56) References Cited

U.S. PATENT DOCUMENTS

| 2,512,857 A | 6/1950 | Gow |
| 3,474,660 A | 10/1969 | Dooley |
| 2015/0052974 A1* | 2/2015 | Pieczarek ............. G01N 25/18 73/25.03 |
| 2015/0219578 A1* | 8/2015 | Gellert ................... G01N 27/18 73/25.03 |

FOREIGN PATENT DOCUMENTS

| DE | 10318450 | 7/2004 |
| WO | WO 2009/095494 | 8/2009 |

OTHER PUBLICATIONS

German Office Action dated Apr. 11, 2016 corresponding to Application No. DE 10 2015 210 548.2.

* cited by examiner

*Primary Examiner* — Manish S Shah
*Assistant Examiner* — Irving A Campbell
(74) *Attorney, Agent, or Firm* — Cozen O'Connor

(57) ABSTRACT

A detector arrangement to be scaled or adapted in a simple manner depending on the application includes n·m (n≥2, m≥2) thermal conductivity detectors that are each arranged in a mounting on a detector block having a high thermal conductivity, wherein each case m detector block is secured radially symmetrically and spaced apart from one another on a carrier having a central opening, forming a detector module, and n detector modules are located on a common axis by the central openings of the carriers.

7 Claims, 1 Drawing Sheet

DETECTOR ARRANGEMENT

BACKGROUND OF THE INVENTION

1. Field of the Invention

The invention relates to an arrangement of thermal conductivity detectors that requires a minimum of space and is thermally symmetrical.

2. Description of the Related Art

Thermal conductivity detectors are used to detect certain liquid or gaseous substances (fluids) based on the thermal conductivity typical of the substance, and are particularly employed in gas chromatography. To this end, after the substances to be detected have been chromatographically separated they are fed one after the other in a measuring channel past an electrically heated heating filament arranged therein where, depending on the thermal conductivity of the substance flowing past, more or less heat from the heating filament is dissipated onto the channel wall and the heating filament is correspondingly cooled to a greater or lesser extent. As a result of the heating filament cooling down, its electrical resistance changes, which change is detected. To this end, the heating filament is normally arranged in a measuring bridge that contains further resistances and a further heating filament in a reference channel through which a reference fluid flows. Instead of the resistances, further heating filaments can be provided that are arranged fluidically parallel or in series with the heating filaments in the measuring channel or reference channel.

In the following, the term thermal conductivity detector is in each case used for a heating filament and the channel section surrounding the heating filament.

In order to maintain the thermal conductivity detectors used in a measuring bridge at the same temperature level, it is known, for example, from U.S. Pat. No. 2,512,857, U.S. Pat. No. 3,474,660 or DE 103 18 450 B3 to form the channel sections radially symmetrically around the heating filaments in a detector block that consists of a metal having a high thermal conductivity. The channel sections are furthermore arranged radially symmetrically around a central axis of the detector block to obtain a thermal symmetry.

As is known, for example, from WO 2009/095494 A1, thermal conductivity detectors can also be formed in a micromechanically produced component that can then be arranged in a recess in the detector block.

Depending on the application and complexity of the separating column switching or in the case of a plurality of analysis trains, a differing number of thermal conductivity detectors may be required in a gas chromatograph, where the detectors have hitherto been incorporated individually or as detector modules each having a plurality of thermal conductivity detectors in a detector block at different locations of the gas chromatograph.

SUMMARY OF THE INVENTION

It is an object of the present invention to provide an arrangement of thermal conductivity detectors to be scaled or adapted in a simple manner depending on the application, where the arrangement moreover requires a minimum amount of space and is thermally symmetrical.

This and other objects and advantages are achieved in accordance with the invention by a detector arrangement having n·m (n≥2, m≥2) thermal conductivity detectors which are each arranged in a mounting on a detector block having a high thermal conductivity to form a detector module, where each of the m detector blocks are secured radially symmetrically and spaced apart from one another on a carrier having a central opening, and n detector modules are located on a common axis by the central openings of the carriers.

The detector arrangement in accordance with the invention therefore consists of a stack of two or more radial-symmetric detector modules that are located on a common axis to form the stack. The detector blocks of a module with the thermal conductivity detectors contained therein are spaced apart from one another so that no direct transfer of heat from one thermal conductivity detector to the respective adjacent thermal conductivity detector is possible. To this end, the carrier preferably has a hub, containing a central opening, with wings or spokes upon which the detector blocks of the respective module are secured. In order to provide thermal symmetry the carrier can also consist of a material having a high thermal conductivity or be form in one single piece with each detector block secured thereon in each case, such that the thermal path from one of the detector blocks via the hub to each of the other detector blocks of the module is equally as long in each case.

The carriers of immediately adjacent detector modules can advantageously be offset to one another at an angle that is less than or preferably equal to half the angular distance between the detector blocks of a detector module. This ensures that the detector blocks of the stack are set to a gap, which means that with the exception of the side by way of which a detector block is mounted on the carrier all the other sides of the detector block are accessible for the electrical and fluidic connection of the thermal conductivity detector.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention reference is made in the following to the figures of the drawings, in which.

DETAILED DESCRIPTION OF THE EXEMPLARY EMBODIMENTS

Figure 1:
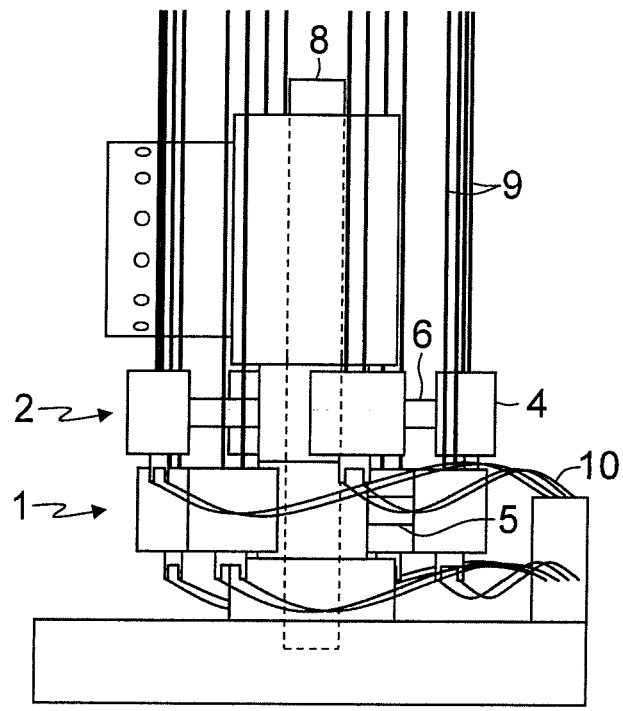
FIG. 1 shows a side view of an exemplary embodiment of the detector arrangement in accordance with the invention.
Figure 2:
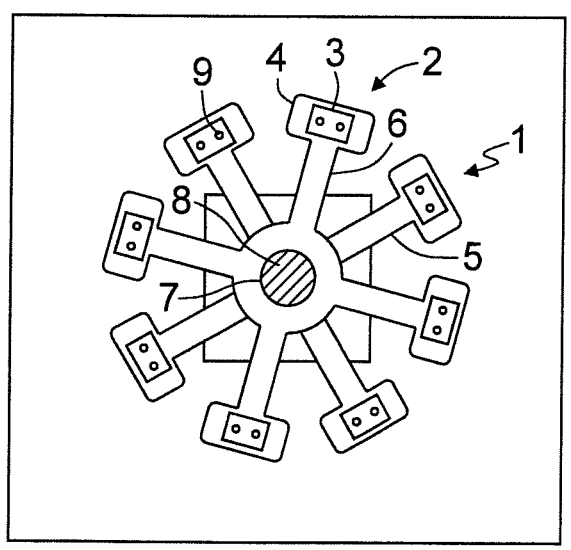
FIG. 2 shows a top, plan view of the detector arrangement of FIG. 1.

FIGS. 1 and 2 show schematic illustrations of a detector arrangement which consists of n, here n=2, detector modules 1, 2 each having m, here m=4, thermal conductivity detectors 3. Each thermal conductivity detector 3 is arranged in a mounting on a respective detector block 4 that consists of a metal having a high thermal conductivity. The four detector blocks 4 of each detector module 1, 2 are secured radially symmetrically and spaced apart from one another on a carrier 5 or 6. The carrier 5, 6 has a hub with a central opening 7, and blades or spokes upon which the respective detector blocks 4 are secured. The detector modules 1, 2 are located by the central openings 7 of their respective carrier 5, 6 on a common axis 8 and, with further attachable detector modules where applicable, form a stack. By offsetting the detector modules 1, 2 at an angle of here 45° to one another (in other words half the angular distance of 90° between the detector blocks 4 of the detector modules 1 or 2) the detector blocks 4 are set to a gap and are easily accessible. Thus, in the case of the exemplary embodiment shown. Here, the fluidic connections 9 of all the thermal conductivity detectors 3 are each arranged on the upper sides and the electrical connections 10 on the lower sides of the detector blocks 4.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A detector arrangement having nm thermal conductivity detectors and n detector modules, wherein n≥2 and m≥2 and the thermal conductivity detectors are each arranged in a mounting on a respective one of detector blocks having a high thermal conductivity; wherein each m detector blocks is secured radially symmetrically and spaced apart from one another on a respective carrier to form a respective detector module, the respective detector module including a respective central opening; and wherein the n detector modules are located on a common axis via the respective central opening of each respective carrier.

2. The detector arrangement as claimed in claim 1, wherein each respective carrier includes a hub, containing the respective central opening, the m detector blocks being secured on wings or spokes on the hub.

3. The detector arrangement as claimed in claim 2, wherein each respective carrier consists of a material having a high thermal conductivity.

4. The detector arrangement as claimed in claim 1, wherein each respective carrier consists of a material having a high thermal conductivity.

5. The detector arrangement as claimed in claim 4, wherein each respective carrier and the detector blocks secured thereon are formed in one single piece.

6. The detector arrangement as claimed in claim 1, wherein each respective carrier of immediately adjacent detector modules are each offset to one another at an angle which is less than or equal to half the angular distance between the m detector blocks of a detector module.

7. The detector arrangement as claimed in claim 1, wherein each detector module has m=4 detector blocks.

* * * * *